(12) United States Patent
Stennert et al.

(10) Patent No.: US 6,241,767 B1
(45) Date of Patent: Jun. 5, 2001

(54) MIDDLE EAR PROSTHESIS

(76) Inventors: Eberhard Stennert, Othegravenstrasse 1, 50935 Köln; Martin Walger, Brentenstrasse 22, 50354 Hürth; Hartmut Meister, Longericher Strasse 31, 50739 Köln, all of (DE)

(*) Notice: Subject to any disclaimer, the term of this patent is extended or adjusted under 35 U.S.C. 154(b) by 0 days.

(21) Appl. No.: 09/341,791
(22) PCT Filed: Jan. 10, 1998
(86) PCT No.: PCT/DE98/00073
  § 371 Date: Jul. 13, 1999
  § 102(e) Date: Jul. 13, 1999
(87) PCT Pub. No.: WO98/30175
  PCT Pub. Date: Jul. 16, 1998

(30) Foreign Application Priority Data

Jan. 13, 1997 (DE) ............................................. 197 00 813

(51) Int. Cl.⁷ .................................................. A61F 2/18
(52) U.S. Cl. ........................................................ 623/10
(58) Field of Search ................................................. 623/10

(56) References Cited

U.S. PATENT DOCUMENTS

| 2,191,832 | * | 2/1940 | Aaugustus | 623/10 |
| 3,712,962 | * | 1/1973 | Epley | 623/10 |
| 4,169,292 | * | 10/1979 | Grote | 623/10 |
| 4,957,507 | * | 9/1990 | Lenkauska | 623/10 |

FOREIGN PATENT DOCUMENTS

| 4407847 | * | 9/1994 | (DE) | 623/10 |
| 0460354 | * | 12/1991 | (EP) | 623/10 |

* cited by examiner

Primary Examiner—David Isabella
(74) Attorney, Agent, or Firm—Trexler, Bushnell, Giangiorgi, Blackstone & Marr, Ltd.

(57) ABSTRACT

The invention relates to a middle ear prosthesis comprising an artificial ear drum (20) and a tubular housing which is tightly joined to said ear drum. The housing consists of a coupling element (28) and a transmitting element (22). The coupling element (28) comprises firstly an open end area (30), configured for resting against the tympanic wall (32) of an ear, and secondly, inside its inner space, a retaining device (34) for a first ossicle part (26) which extends through a small, artificially created opening (36) in the stapes baseplate (38). The transmitting element (22) is connected to the ear drum (20), on the inner surface of which is attached a second ossicle part (24), which comes into contact with and is connected to the first ossicle part (26) when the coupling element (28) and transmitting element (22) are put together.

11 Claims, 3 Drawing Sheets

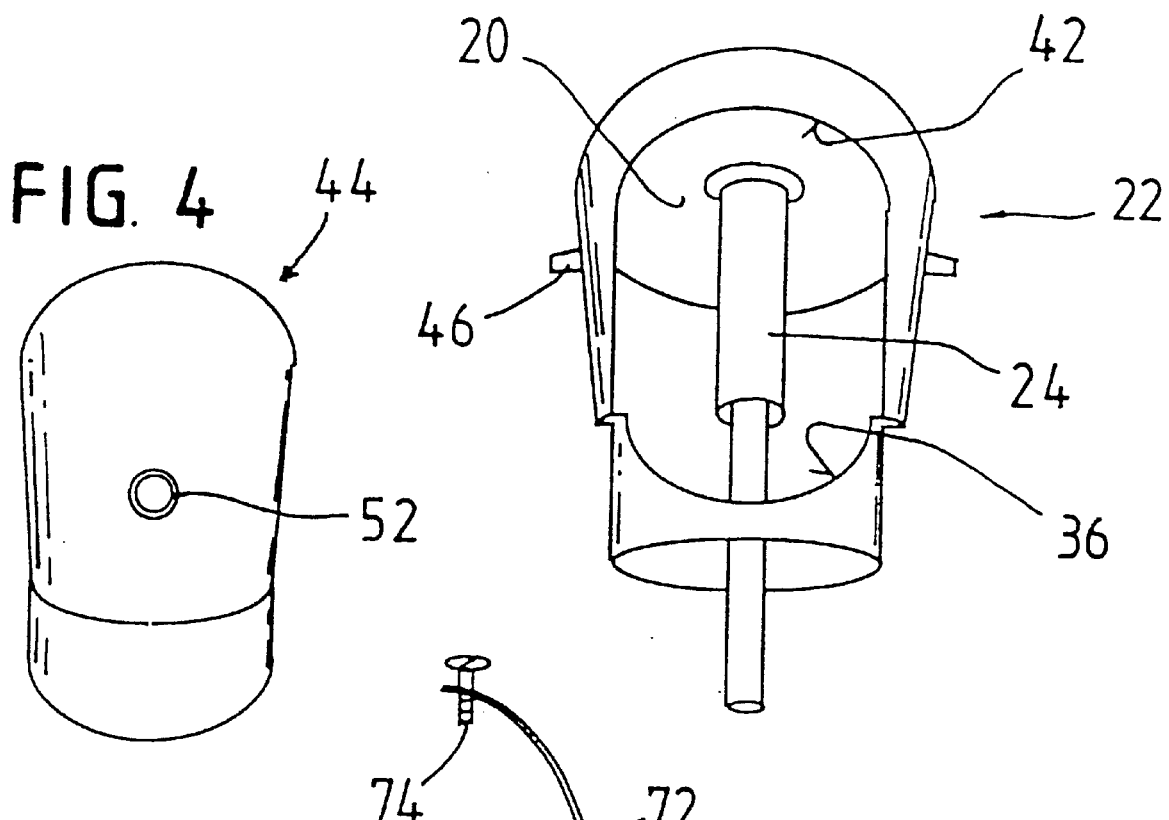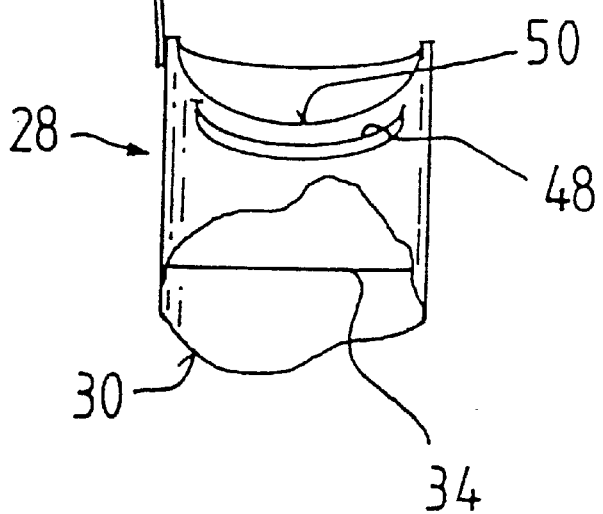

MIDDLE EAR PROSTHESIS

BACKGROUND AND SUMMARY OF THE INVENTION

1. Field of the Invention

The invention relates to a middle ear prosthesis with a tubular housing. The prosthesis replaces eardrum (tympanic membrane) and ossicles of the middle ear which have been destroyed by otitis or similar.

2. Description of the Prior Art

It is presently known to repair the sound receiving and conducting mechanismus of the middle ear by surgical implantation of various types of prosthesis. Such repair involves total reconstruction of all three ossicles and the ear drum.

Such a middle ear prosthesis is known out of DE 4 407 847 A1. The tubular housing of this prosthesis is not only closed at its outwards showing end by an outer membrane replacing the eardrum. It is also provided at its inner end with an inner membrane. Said inner membrane is joined to the outer membrane by a transmission link that is located inside and that prestresses inwards outer and inner membrane. The surface of the outer membrane is bigger than the surface of the inner membrane. Sound transmission from the inner membrane to the stapes base plate occurs by a small quantity of the patient's own fat. This fat required for sound transmission is located outside the prosthesis between the inner membrane and the stapes base plate.

A disadvantage of this known middle ear prosthesis is that the achievable sound pressure at the stapes base plate is not high enough for normal hearing, since the transformation ratio of the two membranes is reduced. Furtheron the transmission path of the sound between the inner membrane and stapes base plate is subject to unsteadiness since the smallest inclusion of air in the fat or its dwindling and the thus occurring smallest air gap are already strongly influencing the transmission of sound.

EP 460 354 B1 discloses a middle ear prosthesis that does without its own housing. The artificial eardrum is tentered in an outer retaining ring inserted in a recess made especially for said ring in the petrous bone. The eardrum has a hole in its centre into which a thickened front area of an ossicle-substitute may be fitted. Thus, the ossicle-substitute may in a first place be arranged in the space behind the artificial eardrum. Then, the artificial eardrum is inserted, whereas the front end of the ossicle-substitute snaps into the hole of the eardrum.

Further middle ear prostheses are known out of EP 281 047 B1, DE 2 905 183 C3, DE 2 937 842 C3 and EP 203 785 B1.

SUMMARY OF THE INVENTION

The present invention overcomes the mentioned problems with the middle ear prosthesis by providing that the sound pressure prevailing in the inner ear is sufficient and that the sound transmission to the inner ear is guaranteed to be always secure and durable.

The middle ear prosthesis according to the invention replaces the function of the sound transmitting apparatus of a natural middle ear as completely as possible. It is hereby not depending on the function of the natural eustachian tube and/or the mucosa of the middle ear cavities.

The middle ear prosthesis according to the invention is used in the attendance of patients with chronic otitis media that durably weakens or hinders a normal sound transmission. Other afflictions with said same consequence are for example mucosal suppuration in the middle ear, suppuration of the bone in the middle ear (=suppuration of a cholesteatoma), chronic perturbation in the aeration of the auditory tube, malformations of the middle ear, permanent destructions of the sound conducting apparatus by trauma and tumours, etc. The middle ear prosthesis is depending neither on a mucosa lining nor on an aeration of the auditory tube. It consists of a housing divided for example in two parts that may at least be closed so as to be germ-tight. The inner space of the housing is thus safe against germs trying to penetrate from the outside.

The housing is provided with a holding device that temporarily fastens the ossicle part called hereinafter first ossicle part. Said holding device is removed, cut apart or otherwise discharged later, before the operation comes to an end. It may also be kept if it is flexible enough.

The first ossicle part is inserted through an artificial opening in the stapes base plate and directly stimulates the inner ear or it is placed onto this base plate. The direct sound transmission to the inner ear is thus assured. The loss of coupling fat or the like can no more be detrimental to said sound transmission.

The first ossicle part is moved by the artificial ear drum and/or by an electric actuation, particularly an electrodynamic or piezoelectric actuation. Such an electric actuation gets its tension from an amplifier, for example from the amplifier of a hearing aid.

During the operation, the inner space of the housing may be reached through the window. It allows the necessary manipulations inside the housing. Particularly the holding device may be reached through the window. Said window is closed by the cover part so as to be germ-tight.

The window may have different versions. The window may for example be provided between two parts of a housing consisting of a transmission part and a coupling part, whereas recesses or indentations on the edge side are provided in the overlapping area of the two parts. Said recesses are forming the window when positioned in a certain rotary position relative to one another, whereas, in another rotary position, they are closing completely. Housings consisting of three and more parts are also possible, the third and possibly further parts being allocated for constituting or locking a window area, for example by an axial slidable cylinder. Annular, cylindrical parts that are rotatable relative to the coupling part and/or transmission part and that have a window just as said part are also provided. The window may be either released or completely locked by rotation.

During the operative insertion of the middle ear prosthesis, the coupling part is inserted first and is attached in the best possible way to the wall of the eardrum around the oval window. It has proved to be particularly preferential to imitate as accurately as possible the course of the individual relief of the medial eardrum wall of the patient wearing the middle ear prosthesis when designing the free end area of the coupling part. A good adaptation to the eardrum wall is thus achieved which makes it possible to obtain, using appropriate connecting material, a proper closing and a secure fastening of the coupling part on the eardrum wall.

When the coupling part is inserted, in case of an opening in the stapes base plate, said opening is either already provided or it is arranged only then. It is preferably made by means of a laser. It is just big enough for the first ossicle part to fit through it. The first ossicle part is preferably a thin wire made of titanium or gold. The first ossicle part is fixed on the holding device or has already been fixed to it. The fixation is made in such a way that the first ossicle part is projecting into the inner ear to a desired extent. The fixation guarantees that the projection will neither fall short of nor exceed said extent.

It has proven to be particularly advantageous for the housing of the middle ear prosthesis according to the invention to seal the surrounding tissue in a germ-tight, preferably hermetic way. Thus, the inner space of the housing is securely protected against the penetration of germs.

The location and size of the housing of the middle ear prosthesis have well enough been determined by considerable measurements done on petrous bone preparations. Typically, an average maximal diameter of approximately 11 mm and a maximum length of approximately 20 mm have been found.

The housing preferably consists of the coupling part and of a transmission part, both being provided with connecting means for their junction to one another and to the housing. The transmission part is preferably provided with a second ossicle part. During the operational insertion, the connection between the two ossicle parts may be observed and preferably executed through the window.

For the implantation of the middle ear prosthesis, it has proven to be of advantage to provide the housing with connecting means for the mechanical fixation of the housing on the petrous bone of the wearer. Although it is possible and even desired to fill out the space of the middle ear around the prosthesis in order for the prosthesis to have a good seat, the mechanical anchorage in the bone guarantees a durable secure fixation during the operation and also later, in case of impacts.

When the middle ear prosthesis is provided with an eardrum, it has proven to be preferable to arrange the eardrum in an angle to the axis of the housing. The bigger said angle has been chosen, the bigger the surface of the eardrum. Angles of between 40° and 80° to the axis of the transmission part, and particularly an angle of approximately 53° have proven to be advantageous. The preferred artificial eardrum has thus got an out-of-round shape, particularly an elliptic one. Resonances are thus avoided. The big surface for sound pick-up is particularly advantageous. Surfaces of approximately 100 square millimeters are typically obtained.

For the second ossicle part, commercial parts may be used, for example the ossicle surrogate offered for sale by the enterprise Richards GmbH under the trade name TILT-TORP-PORP. It has a drilled shank into which the first ossicle part may be inserted. On its other end it has a ball-and-socket joint that allows compensating movements. Thus, a largely cylindrical, essentially one-dimensional movement may be transmitted to the inner ear liquid. A new prosthesis part may also be developed as second ossicle part that meets the requirements of this mechanical principle.

Since the middle ear prosthesis according to the invention has, when inserted, an essentially hermetically sealed inner space, the middle ear spaces are not aerated as they are in nature by the eustachian tube. When the actuation is purely electrical, pressure compensation is not necessary. If the prosthesis is provided with an eardrum, an artificial pressure compensation device is indispensable. It consists of an outer part that is accessible from the outside and that is hidden for example behind the ear in a way similar to the bone-anchored hearing aids working on body sound, and of an inner part that is located for example in the mastoid. This inner part has, in a first embodiment, a fine strainer, particularly a strainer blocking any kind of microbes and viruses. The material used for said strainer particularly consists in hollow fibres. Alternatively, the inner part may also have a pressure compensating membrane. Hereby, a flexible membrane is tentered in an own housing in a completely tight way, whereas it constitutes an absolute barrier between an outer chamber connected to the outer world and an inner chamber connected to the inner space of the prosthesis. Outer part, inner part and middle ear prosthesis are linked together by means of thin tubes, particularly silicone tubes, in a tight and durable way.

In order to take hold of the individual relief of the eardrum wall of a wearer and consequently to be able to provide the free end area of the coupling part with the desired shape or profile, several possibilities are available. Said shape may be obtained by a high-resolution spiral scanner and be directly transmitted via an intermediate stage of a processing machine for the free end area. On the other hand, the relief may also be scanned by means of direct measurements with rays, whereas the processing machine may be accordingly actuated directly or indirectly. The shape may also be scanned mechanically, a proper scanning apparatus having been developed to that purpose. The data obtained with this scanning apparatus may be used for the actuation of a processing machine.

Further advantages and characteristics of the invention will become clear in the remaining claims and in the following description of embodiments that are only examples and are not limiting the scope of the invention. Said embodiments are explained in more detail with the aid of the drawing.

BRIEF DESCRIPTION OF THE DRAWINGS

FIG. 2: shows an exploded view of a transmission part with a view on and through an operational window, FIG. 3: shows a representation of a coupling part according to the representation according to FIG. 2, FIG. 4: shows a top view on a cover plate.

DESCRIPTION OF THE PREFERRED EMBODIMENTS

Figure 1:
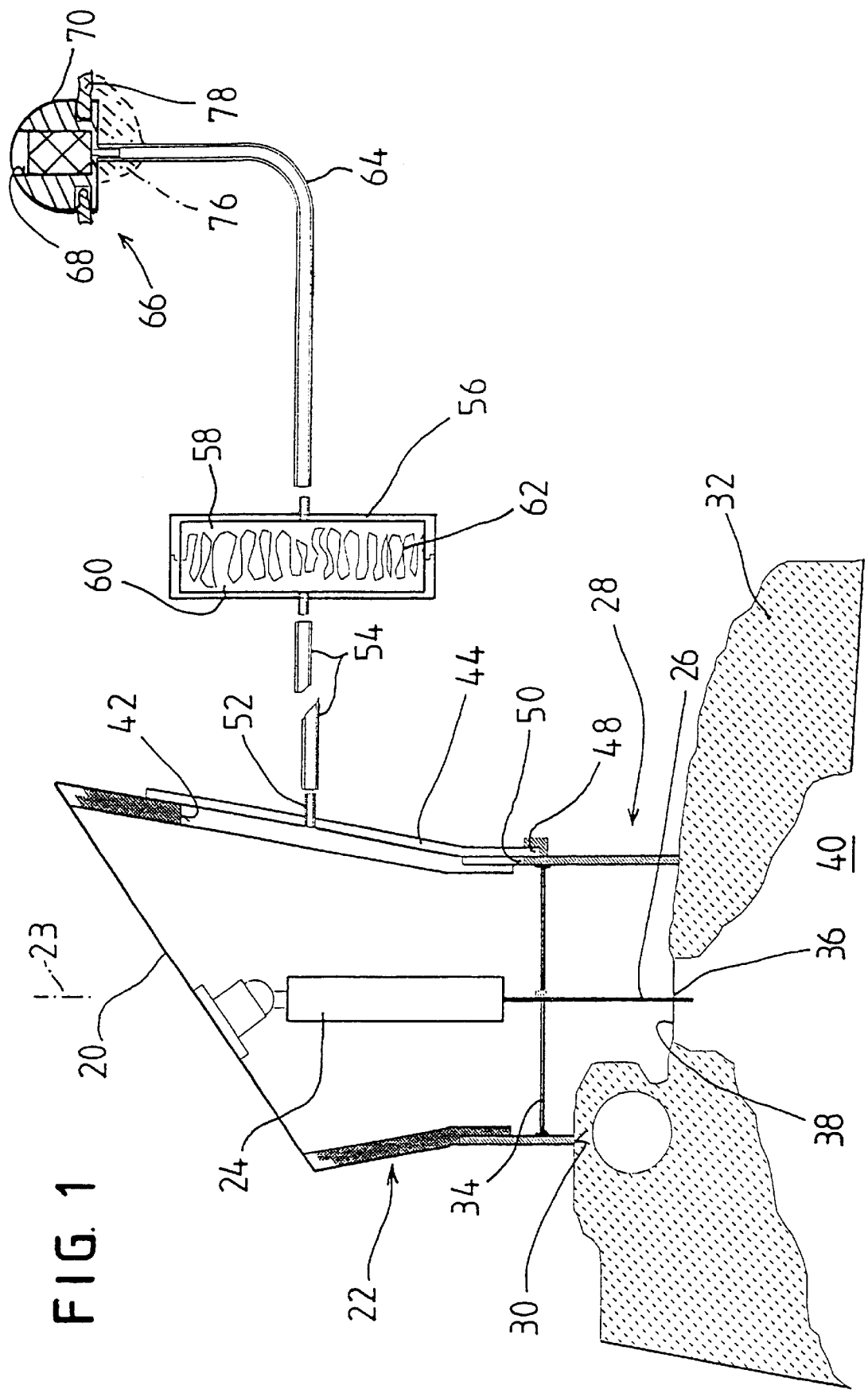
FIG. 1: shows a sectional drawing of a middle ear prosthesis with an added pressure compensating device.

The middle ear prosthesis of a first embodiment shown in FIGS. 1 to 4 has an artificial eardrum 20 that has an essentially oval blank. Its surface is bigger than the surface of a normal human eardrum (tympanic membrane), for example 1.5 times bigger. It is cut in a material that is biologically appropriate for the use as a prosthesis, more particularly in the material Millicell HA of the enterprise Millipore GmbH, in GORE-TEX 0.1 mm of the enterprise W. L. Gore & Assoc. GmbH or in flexible silicone. Millicell, Millipore, GORE-TEX and Gore are protected trade marks. In practical use, the eardrum 20 is epithelized.

The eardrum 20 is tightly connected with a housing that is, in the embodiments shown in the FIGS. 1 to 4 and 5, divided into two parts. The eardrum 20 is connected to a transmission part 22. The latter has an essentially cylindrical area shown in the lower part of FIG. 2 and an area that is widening, starting from said cylindrical area and essentially running on an envelope of cone. The diameter of the cylindrical area is of approximately 8 mm. The widening area has corresponding measurements of approximately 11 mm. As FIG. 1 particularly shows, the eardrum 20 is located on one level, it runs in an angle of 35° to a longitudinal axis 23 of the transmission part 22. Thanks to the inclination of the eardrum 20, said eardrum 20 has a bigger surface than the natural eardrum.

On the inner side of the eardrum 20, preferably on the centre of the surface, a second ossicle part 24 is durably fastened. In the embodiment of FIGS. 1 to 4 a commercial ossicle surrogate of the enterprise Richards GmbH is used. In the vicinity of the eardrum 20 it has a ball-and-socket joint. Underneath said ball-and-socket joint a hollow shank receives a first ossicle part 26 that still has to be discussed. The second ossicle part 24 runs underneath the ball-and-socket joint centrically to the centre line of the transmission part 22.

The housing also has a coupling part 28. It is as a whole a bit smaller than the transmission part 22 and is designed together with said transmission part 22 in such a way that both parts may be connected to one another in an easy, tight and durable way. This may particularly be achieved by insertion in longitudinal direction and by glueing. The coupling part 28 is essentially cylindrical. Its diameter is of approximately 6 mm, too. It has a free end area 30 that has a shape imitating as exactly as possible the individual relief of the eardrum wall of a wearer of the middle ear prosthesis. The thus resulting, individual shape may particularly be seen in FIG. 3. As already explained above, several methods may be used to acquire or scan the shape of the individual relief of the eardrum wall. Reference is made to the patent application "Device for the mechanical scanning and acquisition of the eardrum shape of a middle ear" of the same applicant and of the same application date. The content disclosed in this application is made part of the content disclosed in the present application.

The free end area 30 is accordingly designed in such a way that it sits close to the eardrum 32, as may be seen in FIG. 1. A tight-sealed closure may thus be achieved, liquid fixing and sealing agents may be used to connect the free end area 30 and the eardrum 32.

In the coupling part 28, a holding device 34 is provided for the first ossicle part 26. Said ossicle part 26 is designed as a thin golden wire that closely fits through a very small, artificially provided opening 36 in a stapes base plate 38, thus projecting with its lower, free end area into the inner ear 40. In the embodiment shown, the holding device 34 is an essentially diagonally running wire on which the first ossicle part 26 is fastened or may be fastened. During the implantation of the middle ear prosthesis, the holding device 34 is cut through so that the first ossicle part 26, which is connected to the second ossicle part 24, may move freely back and forth through said holding device.

In all the three embodiments shown of the middle ear prosthesis, an access to the inner space is necessary for the connection of the two ossicle parts 24, 26 as well as for the cutting through of the holding device 34. Other constructions with no such access are possible. For said access, a window 42 is provided in the transmission part 22. This window 42 may be closed by a cover plate 44 as shown in FIG. 4. Appropriate mechanical holding means are provided in order to ensure an accurate and tight fastening of the cover plate 44 on the transmission part 22 and on the coupling part 28. In the embodiment shown, mandrels 46 are provided to fasten the cover plate 44, the coupling part 28 is provided with a groove 48 formed by a projecting part and meant to receive the cover plate 44. As shown in FIG. 3, the coupling part 28 too preferably has a recess 50 in its upper area, said recess being also designated as the lower window bay.

As shown in FIG. 4, the cover plate 44 has a connection 52. Said connection is assigned to a tube 54, both may be seen in FIG. 1. The tube 54 is leading to an inner part 56 of a pressure equalizing device. Said inner part 56 is designed as a boxlike housing. It has two chambers, namely an outer chamber 58 and an inner chamber 60. Both are hermetically separated from one another by a very flexible membrane 62. In another embodiment, they are separated from one another by a fine filter sealed against bacteria and microbes but permeable to air. The fine filters that may be used here are particularly hollow fibre filters.

The outer chamber 58 is connected to an outer part 66 via another tube 64. It is anchored in a bone 76 and is in parts accessible from the outside, see skin 78. The construction used here is quite similar to the one used with so-called bone conducting hearing aids. The outer part 66 has a recess 68 into which a strainer 70 is inserted. Said strainer is preferably exchangeable. The strainer 70 hinders water, coarse dirt and the like to penetrate the tube 64. The barrier against germs and the like is assured by either the membrane 62 or by the fine filter that replaces said membrane. Reference is made to the application of the same applicant with same application date "Pressure-equalizing device as a prosthetic replacement for a eustachian tube". The content disclosed in this application is also part of the content disclosed in the present invention, For the parts 22, 26, 28 and 44 as well as for 56, 66, titanium is the material that is best suitable. According to FIG. 3, a strap-joint 72 fastened on the coupling part allows the fastening on the petrous bone. A screw 74 is provided to that purpose.

Figure 5:
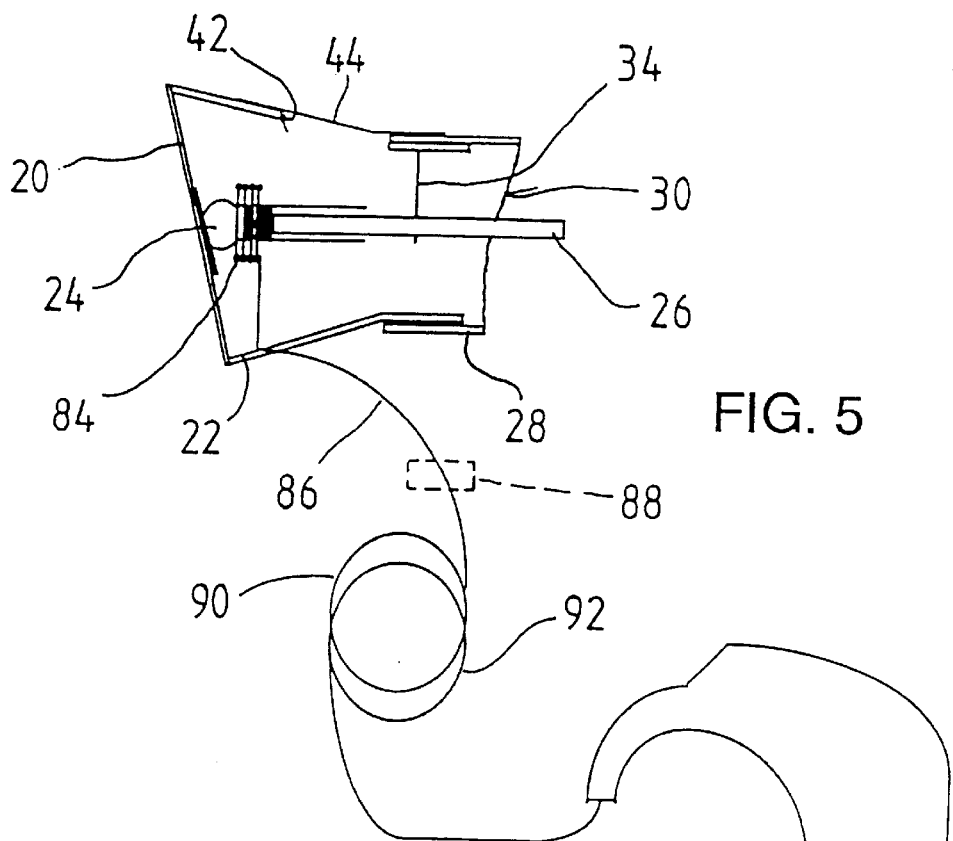
FIG. 5: is a sectional drawing of a housing in a view similar to the one in FIG. 1, but now with an additional electrodynamic actuation and with an external amplifier connected via a transmission link

In the second embodiment represented in FIG. 5, a housing with an artificial eardrum 20 is used, said housing corresponding to the housing of the first embodiment. The modification compared to the first embodiment is that a ferromagnetic core 82, more particularly a core made of a ferrite material, is provided in the tube-like guidance of the second ossicle part 24. Around the area of the second ossicle part 24 outside the core 82, a coil 84 that is connected to the housing is mounted. The second ossicle part 24 is made of a synthetic material or of another, non-conductive material. Coil 84 and core 82 are constituting together an electrodynamic actuation. The coil 84 is connected with a secondary coil 90 of a transformer via a supply tube 86 and possibly with the help of the connection in series of an implanted amplifier 88. The secondary coil 90 is located underneath the skin 78, whereas the corresponding primary coil 92 is located outside the skin 78. The primary coil 92 is connected to the output of a hearing aid 94.

In practical operation, a microphone inserted in or assigned to the hearing aid 94 receives sound information. This information is amplified in the hearing aid 94 and, if necessary, processed. The amplified signals are brought to the primary coil 92. From there, they are transmitted to the secondary coil 90 and thus to the coil 84.

In order to improve the power transfer of the transformer 90, 92, converting the sound information in the hearing aid 94 into a high frequency band of for example the frequency of one megahertz is advisable. This occurs in a way similar to the carrier frequency technology used in telephone systems or accordingly.

As in the first embodiment, the movement of the eardrum 20 is still transmitted onto the two ossicle parts 24, 26. That means that two movement actuations are active. On one hand, the ossicle parts 24, 26 are moved by the eardrum 20 and thus by the sound arriving directly to the eardrum 20, on the other hand, they are moved by the electrodynamic actuation described above. The electrodynamic actuation may only assist the movement in certain frequency ranges, for example only in the high frequency range of the audible range. The electrodynamic actuation may thus preferably compensate a defective hearing that only concerns certain frequency ranges. The electrodynamic actuation may, however, also be active in the whole frequency range of the audible range.

Figure 6:
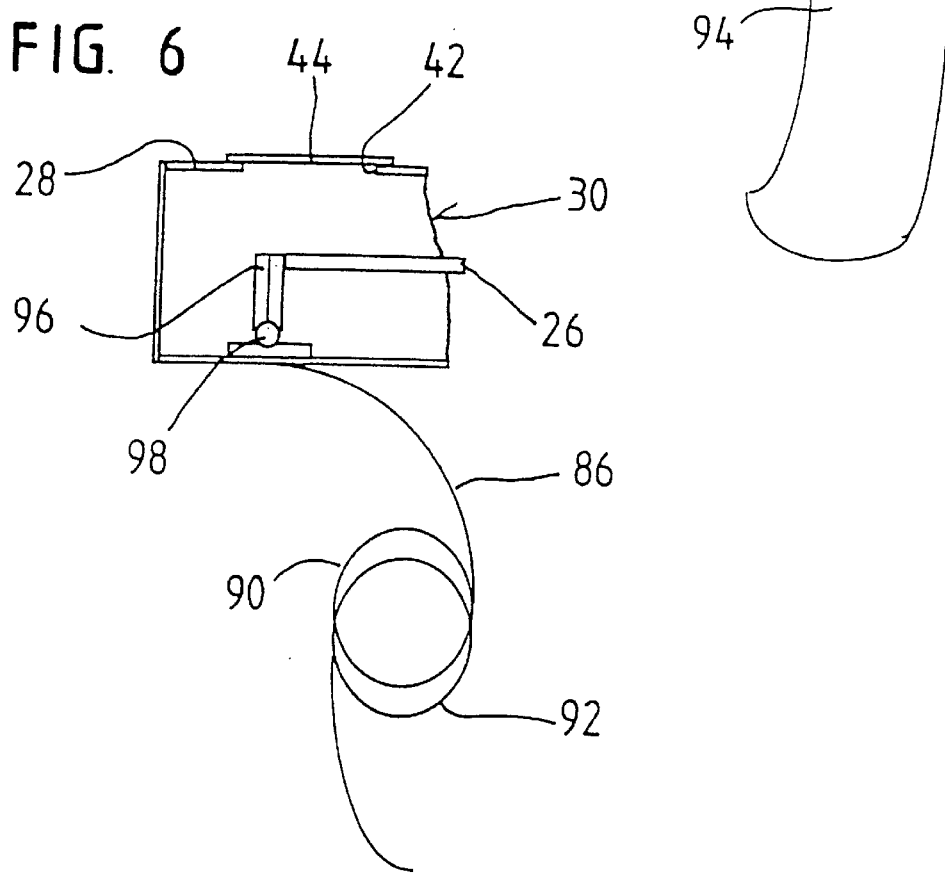
FIG. 6: shows a representation similar to FIG. 5, but without an amplifier and now also without an eardrum, the actuation being exclusively piezoelectric.

In the third embodiment according to FIG. 6, several decisive amendments have been made. The housing is now in one piece, it consists of the coupling part 28 in which the window 42 is provided, said window 42 being covered by the cover plate 44. Instead of an eardrum 20, the housing is tightly closed at its end area opposite the free end area 30. The housing thus has essentially a cupular shape. The closure in the end area may serve as window instead of the represented window 42.

There is only one first ossicle part 26 provided, a second ossicle part has been omitted. The first ossicle part is connected to the inner wall of the coupling part 28 via a piezoelectric element 96 that is running across. A holding device 98 is provided. The piezoelectric element 96 has got the shape of a longish plate designed here as a double plate. When electrically stimulated, it executes movements in the longitudinal direction of the first ossicle part 26. It is connected to the secondary coil 90 of a transformer via the supply tube 86. The transmission and connection to a hearing aid 94 occur in the same way as in the example of an embodiment illustrated in FIG. 5.

As opposed to the example of an embodiment illustrated in FIG. 5, the electric actuation now assumes the complete sound stimulation of the inner ear, since there is no eardrum provided. Selective hearing problems of the wearer of the ear prosthesis may be compensated by making the appropriate arrangements in the hearing aid 94.

What is claimed is:

1. Middle ear prosthesis comprising:
a tubular housing having an axis and defining an inner space and having a closed end area and a free end area, the tubular housing being open at the free end area and being closed at the closed end area, said free end area being individually configured and adapted to fit to and to rest against a medial eardrum wall around a stapes base plate of a patient, said closed end area being closed by one of an artificial eardrum and a closure means, a first ossicle part arranged in the inner space and adapted for transmission of sound to an inner ear of the patient, and a holding device provided in the inner space for holding the first ossicle part relative to the tubular housing, said tubular housing further comprising a window to allow access to the holding device and a coverplate to cover and seal the window.

2. Middle ear prosthesis according to claim 1, wherein the closed end area is closed by an artificial eardrum and a second ossicle part is provided, which is located in the inner space, is connected to the artificial eardrum and is connected to the first ossicle part.

3. Middle ear prosthesis according to claim 2, wherein the artificial eardrum is inclined at an angle of 85° to 40° to the axis of the tubular housing.

4. Middle ear prosthesis according to claim 2, wherein the artificial eardrum is inclined at an angle of 53° to an axis of the tubular housing.

5. Middle ear prosthesis according to claim 2, wherein the artificial eardrum has an elliptic blank.

6. Middle ear prosthesis according to claim 1, wherein an electric actuation means is provided, which electric actuation means is arranged in the housing and is connected to move with the first ossicle part.

7. Middle ear prosthesis according to claim 1, wherein the housing is provided with connecting means adapted for the mechanical fixation of the housing on a bone.

8. Middle ear prosthesis according to claim 1, wherein the first ossicle part is detachably connected to the holding device.

9. Middle ear prosthesis according to claim 1, wherein, when the free end area rests sealingly against the medial eardrum wall the inner space of the tubular housing is sealed against germs.

10. Middle ear prosthesis according to claim 1, wherein a connection is provided to connect the inner space via a tube to a pressure compensating device.

11. Middle ear prosthesis according to claim 1, wherein said housing is composed of a coupling part and a transmission part, the coupling part exhibiting the free and area and the transmission part exhibiting the closed end area.

* * * * *